United States Patent [19]

Stiff

[11] Patent Number: 4,853,157

[45] Date of Patent: Aug. 1, 1989

[54] PROCESS FOR THE MANUFACTURE OF NITRIC ACID ESTERS

[75] Inventor: Anthony J. Stiff, Johannesburg, South Africa

[73] Assignee: AECI Limited, Johannesburg, South Africa

[21] Appl. No.: 620,624

[22] Filed: Jun. 14, 1984

[30] Foreign Application Priority Data

Jun. 24, 1983 [ZA] South Africa .................. 83/4643

[51] Int. Cl.$^4$ .......................................... C07C 77/02
[52] U.S. Cl. ................................... 558/483; 558/484
[58] Field of Search ............... 260/467, 466, 705, 688, 260/701–703, 705; 149/2, 88; 534/601, 887; 560/19, 20, 21–28, 79, 81, 94

[56] References Cited

U.S. PATENT DOCUMENTS

| | | | |
|---|---|---|---|
| 3,111,538 | 11/1963 | Stow | 260/467 |
| 3,331,867 | 7/1967 | Smiley | 260/467 |
| 3,408,388 | 10/1968 | Hagemeyer et al. | 260/467 |
| 4,000,179 | 12/1976 | Ayerst | 260/467 |
| 4,251,455 | 2/1981 | Gebauer | 260/467 |
| 4,352,699 | 10/1982 | Ziegler | 149/109.6 |

FOREIGN PATENT DOCUMENTS 123988 12/1970 India .

OTHER PUBLICATIONS

Russian publication by E. Yu. Orlova, "Khimiyai tekhnologiya brizantnykh vzryvchatykh veshchestv", Khimiya publishing house, 10, 1973, p. 585.
Chemtech–Oct. 1977, pp. 626–629, entitled "Synthetic Housekeeping–Nitration", Chemical Communications, Jul. 1977, pp. 484–485.

Primary Examiner—Barry S. Richman
Assistant Examiner—T. J. Wallen
Attorney, Agent, or Firm—Cushman, Darby & Cushman

[57] ABSTRACT

A process for the preparation of nitric acid esters of organic hydroxy compounds by reacting an organic hydroxy compound with nitric acid in the presence of both sulphuric acid and in a solvent, followed by separating off the spent acid, substantially neutralizing the residual acidity of the organic solution, and removing solvent to leave the organic nitrate. From 95% to 220% of the stoichiometric requirement of nitric acid for complete nitration is used. The mole ratio of water to sulphuric acid at the end of the reaction is from 0.2:1 to 2.5:1. From 200 to 2000 ml of solvent per mole of hydroxy group is present. Yields of at least 92% are obtained. The invention is particularly suitable for the preparation of alkyl nitrates, alkylene or polyalkylene glycol, monoalkyl ether mononitrates, alkylene or polyalkylene glycol dinitrates, diol nitrates, nitrates containing homocyclic or heterocyclic rings, or nitrates derived from polyols.

4 Claims, 4 Drawing Sheets

PROCESS FOR THE MANUFACTURE OF NITRIC ACID ESTERS

This invention relates to processes for the manufacture of nitric acid esters of organic hydroxy compounds, which esters are also known as organic nitrates.

The manufacture of nitric acid esters (i.e. organic compounds containing an —$ONO_2$ group) by reaction of a hydroxyl-containing substance with nitric acid, usually in admixture with sulphuric acid (i.e. as mixed acids), is known. A process involving such a reaction is used commercially for the production of such simple aliphatic nitrate esters as nitroglycerine and ethylene glycol dinitrate. However, such a process is less suitable for more complex or higher molecular weight materials, for example for the production of triethylene glycol dinitrate (TEGDN) and polyethylene glycol dinitrates and other mono- and polyhydric alcohols. This is because the yields obtained by direct nitration with mixed acids tend to decrease with increasing molecular weight, and because the solubility of the nitrates in the spent acids becomes appreciable. This gives rise to spent acids which contain significant proportions of oxidisable organic material, and so tends to decrease the stability of the spent acids.

In a published laboratory proposal for producing nitric acid esters of aliphatic diols in an organic solvent, over 240% of the stoichiometric requirement of nitric acid for complete nitration was used. The mixed spent acid was separated from the solvent and thereafter the solvent was washed and dried, and the nitrate separated from the solvent. Yields of from 23 to 90% were obtained. In addition to the economic problem of providing a yield of only 90%, this proposal has the further disadvantage that there is a large amount of a mixture of highly dangerous spent acids to be dealt with.

A laboratory process for preparing a nitric acid ester of an organic hydroxy compound, such as isoamyl alcohol, is known. In this process, the alcohol is added with carbon tetrachloride as solvent. Only 45 ml of solvent per mole of hydroxy group were used and the yield was about 90%.

Yields of below about 92% are economically not acceptable for the commercial production of nitric acid esters of organic hydroxy compounds.

The present invention provides a process for the preparation of nitric acid esters of organic hydroxy compounds in which at least 92% of the organic hydroxy compound is converted to the nitric acid ester, which process comprises reacting an organic hydroxy compound with nitric acid in an amount of from 96% to 220% of the stoichiometric requirement for complete nitration, in the presence of sulphuric acid in such an amount that the mole ratio of water to sulphuric acid (FWSR) at the end of the reaction is from 0.2:1 to 2.5:1, and in the presence of a solvent which is inert to the reaction conditions in an amount of 200 to 2000 ml per mole of hydroxyl group, followed by separating off the spent acid(s) from the reaction mixture, substantially neutralizing the residual acidity of the organic solution, and removing the solvent to leave the nitric acid ester.

The process of the invention thus includes the steps of (a) nitration, (b) sulphuric acid recovery, (c) nitric acid recovery (when used in excess), (d) neutralization, and (e) solvent recovery. The individual steps are described more fully below. We have found that by working within the conditions specified according to the invention, unexpectedly high yields, and advantages in the recovery of spent acids, are obtained.

The process of the invention enables the nitric acid esters to be prepared in very high yields, typically 98% or more. Due to the large thermal inertia of the solvent, it appears to be safer to operate than conventional mixed acid processes. It produces more stable spent acid streams than conventional mixed acid processes, because of the high yields obtained. One is able to recover spent nitric and sulphuric acids separately when the nitric acid is in excess over the stoichiometric amount.

The process is suitable for the preparation of a wide range of organic nitrates, (i.e. nitric acid esters of organic aliphatic, alicyclic and heterocyclic hydroxy compounds). Examples are alkyl nitrates, which includes such materials as butyl, amyl, hexyl, heptyl, octyl, nonyl and decyl nitrate, as well as isomers thereof, such as 2-ethylbutyl nitrate and 2-ethylhexyl nitrates and the like; alkylene and polyalkylene glycol monoalkyl ether mononitrates, which includes such materials as methoxy, ethoxy, propoxy and butoxy ethyl nitrates, materials such as 2-ethoxy ethyl nitrate, as well as 2'-butoxy-2-ethoxy ethyl nitrate, 1-ethoxy-propyl-2-nitrate, 2'-methoxy-2-ethoxy ethyl nitrate, 1-methoxy-propyl-2-nitrate, 1-butoxy-propyl-2-nitrate, and the like; alkylene or polyalkylene glycol dinitrates, for example diethylene glycol dinitrate (DEGDN) and triethylene glycol dinitrate (TEGDN); diol dinitrates which includes such materials as butane diol dinitrate and the like; nitrates containing homo- and heterocyclic rings, which includes such materials as cyclohexyl nitrate, tetrahydrofurfuryl nitrate, and the like; nitrates derived from polyols, which includes such materials as glycerol/ethylene oxide and glycerol/propylene oxide condensation product nitrates, and the like; and nitrates derived from other mono- and polyhydroxylic materials, including nitrates derived from alcohols already containing nitro and/or ether groups.

The process is well suited to the preparation of poly (oxyethylene) glycol dinitrate oligomers and their mixtures DEGDN, TEGDN, and poly (oxyethylene) glycol dinitrate mixtures.

It is particularly suitable for the preparation of poly (oxyethylene) glycol dinitrate mixtures containing 3 to 10 oxyethylene groups (e.g. in the average molecular weight range 250–500), since the high yield results in little change in oligomer distribution.

Only from 95% to 220% of the stoichiometric amount excess of nitric acid can be present, more usually from 100 to 200% of the stoichiometric amount. We have found that for nitration of poly (oxyethylene) glycols to their corresponding nitric acid esters, nitric acid preferably should be present in approximately 200% of the stoichiometric amount, i.e. about two moles (e.g. 1.8 to 2.2) of $HNO_3$ per mole of hydroxyl group. For nitration of most alkanols, nitric acid preferably should be present in approximately the stoichiometric requirement (e.g. from 1.0 to 1.1 moles nitric acid per mole of hydroxy group, i.e. 100% to 110% of the stoichiometric amount).

The solvent preferably is a halogenated aliphatic organic compound which is inert to the reaction conditions. One preferred solvent is dichloromethane (DCM), which may be present in a quantity of about 200 to 2000 ml (e.g. approximately 500 ml) per mole of hydroxyl-containing substance. Since water is normally present in the acids used, and is generated in the reaction, the quantity of sulphuric acid conveniently should be such that the mole ratio of water to sulphuric acid is less than approximately 2.2 to 1 when all the substance has reacted. When this ratio increases appreciably above 2.2 to 1, the efficiency of the nitration process, as shown by the yield of product, begins to fall off. In some cases, this fall-off occurs at a lower ratio, e.g. approximately 1.2 to 1 in the case of $C_6$ to $C_8$ alkyl nitrates, and the quantity of sulphuric acid should be adjusted accordingly. The reaction is exothermic, and should be controlled at or below ambient temperature. A temperature of about 15° C. is generally suitable. Other solvents that may be used include other halogenated hydrocarbons, such as chloroform.

The conditions of the reaction, including the amounts of reactants and solvent, can be adjusted by experimentation, within the parameters of the invention to give the highest possible yield for a particular hydroxy compound.

Various ways of carrying out the nitration step will now be described.

The organic hydroxy compound to be nitrated may be converted to the nitric acid ester in solution in the solvent, while admixed with the spent acid. This can be carried out either in a batch mode or continuous mode. The advantage of batch production is that control of the reaction is simple while the advantages of continuous production are that reactor inventories are smaller and refrigeration requirements for cooling the reaction are continuous. This means that lower refrigeration capacity is required for a particular production rate.

The nitration solvent conveniently should have a relatively low boiling point. It should be a good solvent for the hydroxy compound and for pure nitric acid. It conveniently should not be a solvent for aqueous compounds such as water and sulphuric acid. It should be stable in the presence of mixed acids and should not form nitric acid esters or nitro-compounds. A preferred solvent is dichloromethane, although other halogenated hydrocarbons, such as chloroform, can also be used.

The amount of solvent used is between 200 and 2000 ml per gram mole of hydroxyl functional group in each gram mole of substrate, that is, 200–2000 ml per mole of hydroxy compound in the case of a monohydric alcohol and 400–4000 ml/mole in the case of a dihydric alcohol. The preferred amount is between 400 and 800 ml/mole of hydroxyl functional group.

The amount of nitric acid used can be between 95% and 220% of the stoichiometric reaction requirement, i.e. 1 mole of 100% nitric acid per mole of hydroxyl functional group in the hydroxy compound. The strength of the nitric acid can be between 40% and 100%, but is preferably 80–100%. When an excess of nitric acid is required, the excess can be recovered by the acid recovery process described below, and recycled to the nitration reactor. The preferred nitric acid usage is in the range 100 to 200% of the stoichiometric reaction requirement.

The amount of sulphuric acid used can be defined by the quantity FWSR (final water to sulphuric acid mole ratio). This is the molar ratio of the total amount of water (from the nitric acid, sulphuric acid, solvent and hydroxy compound, as well as the water produced in the reaction) at the end of reaction, to the total sulphuric acid added as 100% $H_2SO_4$. The amount of water produced in the reaction is one mole of water per mole of hydroxyl functional group. The FWSR can be between 0.2 and 2.5, with typical values being in the range 0.9 to 2.1.

The temperature at which the reaction is carried out can be in the range of −20° C. to +30° C., although typical values are in the range 0° C. to 15° C.

The reaction can be carried out by adding the above-mentioned reactants to the reactor in such a way that the temperature of the mixture remains at a chosen reaction temperature. The reactants can therefore, in principle, be added to the reactor in any order so long as the solvent is not added after the reaction has been completed. However, certain preferred modes of operation are described below.

In the case of batch nitration, three preferred modes of operation are described. In the first mode, the solvent, sulphuric acid and nitric acid are first added to the agitated reactor and cooled to the chosen reaction temperature. The hydroxy compound is then added slowly at such a rate that the cooling of the reactor is just sufficient to remove the heat of reaction and maintain the desired reaction temperature. Best results are obtained when the organic hydroxy material is evenly distributed across the width of the reactor. Cooling can be by means of coils immersed in the reactor, a jacket around the reactor, or by an external heat exchanger through which the reactor contents are circulated by means of a pump. Cooling can be provided by a chilled liquid stream, such as brine or preferably the solvent, as in this case a coolant leak will not affect the reaction seriously.

An alternative to the methods of cooling the reaction described above, is to operate the agitated reactor at a vacuum or pressure sufficient to cause the solvent to boil at the required reaction temperature Evaporated solvent is returned to the reactor via a refrigerated vent condenser.

In the second mode of batch nitration, the solvent, sulphuric acid and hydroxy compound can be added to the reactor and the nitric acid fed in at a controlled rate, as with the hydroxy compound in the first mode above. The first mode is preferred, however, as the highly corrosive nature of the nitric acid requires a more expensive control valve in the second mode.

In a third mode of batch nitration, the hydroxy compound is diluted with some of the solvent, before being added to the reactor in the same way as in the first mode. The advantage of this mode of operation is that dilution of the hydroxy compound has the effect of lowering its local concentration. This can improve the yield in the case of hydroxy compounds that are particularly sensitive to oxidation by the nitrating medium.

A typical batch reactor suitable for this reaction would be a stainless steel vessel with cooling coils and agitated by a turbine agitator. The agitation must be sufficient to achieve dispersion of the aqueous (chiefly sulphuric acid, but possibly also some unreacted hydroxy compound) phase in the organic (solvent, product, unreacted hydroxy compound and nitric acid) phase. Typically, the agitation power required would be 2–4 kW/m3 of reactor.

In the case of continuous nitration, there is also a range of modes of operation, depending on the way in which the reactants are premixed. However, there are three main ways of operating the nitration.

In the first mode of continuous nitration, the feed nitric and sulphuric acids can be mixed and cooled, and the solvent and hydroxy compound separately mixed and cooled. These two mixtures are then metered precisely to the reactor as streams. The reactor may be a static mixer in a pipeline, followed by a hold-up section, which is cooled. The hold-up section provides an extended contact time between the reactants to allow the reaction to go to completion. This hold-up section can be either a cooled and agitated vessel providing a suitable residence time, or a jacketed pipe with static mixer elements in the tubes. The first option is preferable. The reactor may also take the form of a continuous stirred tank reactor (CSTR) or several CSTR's in series. The CSTR's are cooled and are sized to provide a suitable residence time.

The second mode of continuous nitration involves mixing the solvent, nitric acid and hydroxy compound and then metering this mixture and the sulphuric acid to the reactor, as in the first mode.

The third mode of continuous nitration involves metering all the precooled reactants to the reactor separately. The other features of this mode are the same as the previous two modes of continuous operation.

Generally speaking, for the acid recovery step (b), spent acid, comprising substantially strong sulphuric acid, may be removed by allowing the mixture to settle and separating off the acid phase. Some water may be added before separation if required, to remove a slightly less strong spent acid. The majority of any excess nitric acid present remains in the organic phase, and may be removed by addition of water to extract this acid. After mixing and settling, a spent acid comprising substantially only nitric acid, may be separated. Its strength is dependent on the quantity of water added. Separation of approximately 40% nitric acid is easily achieved, but this strength may be varied by adjusting the water quantity.

Further details of the acid recovery step will now be described.

In this step, the product (the organic nitrate), dissolved in solvent, is separated from the spent acids arising from the reaction step. Either of two major acid recovery techniques can be used.

The first technique is a strong acid separation technique, whereby the spent nitric acid and sulphuric acids are recovered separately. The second is total acid dump, whereby the spent acids are recovered as a mixed stream. The details to be used with these techniques depend on the extent of the nitric acid excess used in the nitration. Prior to the acid recovery step, a dilution step can be carried out. In order to quantify the amount of dilution, it is useful to define a quantity, called the 'water to spent sulphuric acid ratio', or WSSA. This quantity is defined as the molar ratio of the total amount of water (from the solvent, sulphuric acid, nitric acid, hydroxy compound, the reaction and the dilution water) after dilution, to the amount of sulphuric acid as 100% $H_2SO_4$ used in the nitration.

The range of WSSA's used is between 0.4 and 50, with preferred values being 0.9 to 3.0 and 12-20, depending on which of the two acid separation techniques described below, is used.

In a strong acid separation technique, the WSSA can be between 0.4 and 3.0, but is preferably between 0.9 and 3.0. The aqueous layer obtained by this technique will consist of 65-90% sulphuric acid, with trace amounts of nitric acid and organic nitrate, as well as small quantities of solvent. The aqueous layer will be denser than the organic layer. Separation of the phases can be accomplished in any suitable phase separation device. The acid separated is stable. By this it is meant that the acid does not undergo any spontaneous exothermic reaction on standing or on heating. It can, however, be subjected to a wash operation, where it is contacted with between 0.5 and 2.0 volumes of the nitration solvent. This operation will remove virtually all of the organic nitrate and nitric acid in the sulphuric acid, and the wash solvent can be recycled to the nitration reactor. This process thus both improves the yield of product and improves the saleability of the spent sulphuric acid. The spent sulphuric acid can be sold as a by-product of the process. This sulphuric acid will typically contain 0.1-2.0% nitric acid, and less than 5% solvent. The solvent can optionally be removed by air-stripping the acid.

The organic layer resulting from the separation will contain substantially all the excess nitric acid used in the nitration. If the excess is less than 5%, it is possible to send this stream to the neutralization step without further processing. If, however, the excess is larger than 5%, the nitric acid can be recovered by a water wash step. This can either be a single-stage water wash or a multi-stage countercurrent wash. The single-stage wash will result in a by-product nitric acid stream of 2 to 20% nitric acid. The counter-current wash will produce a nitric acid stream of 35-65% nitric acid. This acid may be sold as by-product, reconcentrated for re-use or recycled to the nitration reaction. In the event of the nitric acid being sold, the solvent can be removed by air-stripping of the acid. The washing operation can be accomplished in any suitable liquid/liquid extraction equipment.

In a total acid dump technique (which is generally the less preferred technique), the WSSA can be between 3.0 and 50 but is typically from 12-20, and results in an aqueous layer which contains substantially all the excess nitric acid (if the excess is less than 20%), as well as the sulphuric acid. The resulting acid is typically between 20-40% acid, with typically 1% solvent. This acid can be sold as a by-product or neutralized and disposed of. Alternatively, it can be sent to a denitration plant to recover the acids. The acid layer will be less dense than the organic layer and will therefore be the top layer.

If the nitric acid excess is less than 20%, the nitric acid content of the organic layer will be less than 2%, and so the organic layer is separated off and sent to the neutralization step. If a larger excess of nitric acid is used, the organic layer will still contain significant amounts of nitric acid. In this case, a second water wash is required. This will produce a stream containing 2-10% nitric acid which can be used for the first water dump described above. Alternatively, it can be disposed of separately.

Generally speaking, the residual acidity of the product/solvent solution may be neutralized in the neutralization step (d) with a suitable base, or water may be added and a stronger alkali solution used to neutralize the aqueous layer, whilst maintaining agitation. Neutralization with a base can involve aqueous neutralization or organic neutralization.

In aqueous neutralization, the organic solution is neutralized by contacting it with a weak aqueous alkali, which can be 2-5% ammonium hydroxide, sodium carbonate or another water-soluble alkaline material. The preferred alkali is ammonium hydroxide. It has been found that if a weak base is used, better phase separations result after the neutralization. The resulting aqueous phase from the neutralization can be disposed of or, if the total acid dump technique is being used, can be used as the dump water in the acid recovery step described above.

As an alternative, the residual acidity may be neutralized by the addition of an organic alkaline material, such as ethanolamine. This will result in the presence of this compound in the final product. In order to reduce the requirement for neutralizing chemical, the neutralization step may optionally be preceded by a further water wash step to reduce the residual acidity.

The aqueous neutralization is preferable as the product is then uncontaminated.

After separation of the aqueous layer, the solvent should be removed, e.g. by distillation, from the organic phase in step (e). Preferably, this is carried out under vacuum, to avoid the need for high temperatures. It is possible that the product may be required in solution in another solvent. Provided this second solvent has a higher boiling point than the solvent used for nitration, the second solvent may be added to the product solution obtained in the reaction according to the invention, and the solvent used for nitration removed by distillation. In this case, the use of vacuum may or may not be required.

The organic phase from step (d) usually is a homogeneous solution of the product in solvent, typically 10–30%. Four alternative procedures for solvent recovery are described below. They enable the solvent to be recovered and the product to be purified. These are pressure-vacuum stripping, atmospheric-vacuum stripping, atmospheric-air stripping and atmospheric-steam stripping.

In a pressure-vacuum stripping procedure, the solution is pumped to a pressure stripper operating at 5–8 bar (g) and heated to 80°–120° C. by, for example, steam at 120° C. The liquid leaving this stage is typically about 50% solvent, and passes to a vacuum stripper, operating at 5–10 kPa (abs). The vacuum is produced by letting the solvent vapour from the pressure stripper pass through an ejector, to a condenser, which condenses the vapour from both stages.

The stripping can be accomplished in any suitable evaporating equipment, such as, for example, a kettle-type shell and tube boiler, a falling or climbing film evaporator, or a wiped film evaporator. It can also be accomplished in batch mode in a simple agitated and heated pot.

Depending on the vacuum used, the product from this step contains 0.1–2% solvent. This procedure is well suited to continuous operation. Enhanced vacuum can be achieved by using a vacuum compressor to draw solvent vapour from the vacuum stripper, discharging it to the ejector.

In an atmospheric-vacuum stripping procedure, the solution is first boiled at atmospheric pressure at 80°–120° C. The solvent vapour is condensed, using either cooling water or refrigeration. The product from this stripper is then passed to a vacuum stripper operating at 5–10 kPa (abs), which produces a product containing 0.1–2% solvent. The vacuum is produced by a vacuum compressor, which compresses the solvent vapour to atmospheric pressure or higher, and the vapour is condensed in a condenser. Alternatively, the vacuum can be produced by steam ejectors, the mixed steam and solvent being condensed and separated. This procedure is well suited to continuous operation. The strippers used can be any of the types exemplified above.

The product from either of these two stripping procedures can be further purified by removing the remaining solvent by means of air-stripping.

In an atmospheric-air stripping procedure, the solution is first boiled at atmospheric pressure until the temperature reaches 80°–120° C., the solvent being condensed in a condenser. The solution will then contain typically 20% solvent. Then, maintaining the solution at the final boiling temperature, air is sparged through it to strip the remaining solvent from the product. The solvent-laden air is passed to a refrigerated condenser, which recovers some of the solvent. The remaining solvent-laden air is vented to atmosphere, or scrubbed of its solvent, using a suitable absorbing solution. The advantage of this technique of stripping is that vacuum is not required. The equipment used can be any of the types exemplified above.

In an atmospheric-steam stripping technique, the solution is first boiled at atmospheric pressure until the temperature reaches 80°–120° C., the solvent being condensed in a condenser. The resulting solution is then passed to a vacuum stripper operating at 15–50 kPa (abs), and the remaining solvent is stripped off by a combination of heating and the introduction of live steam into the solution. The steam assists the stripping of the solvent, and therefore the vacuum required for the same final product purity is less severe. The mixed steam and solvent vapour are passed to a condenser, condensed and then separated.

The process of the invention can be adapted to either batch or continuous manufacture, or variations and combinations thereof.

BRIEF DESCRIPTION OF THE DRAWINGS

FIGS. 1 and 2 are different apparatus but the same parts have the same numbering.

DETAILED DESCRIPTION OF THE DRAWINGS

Figure 1:
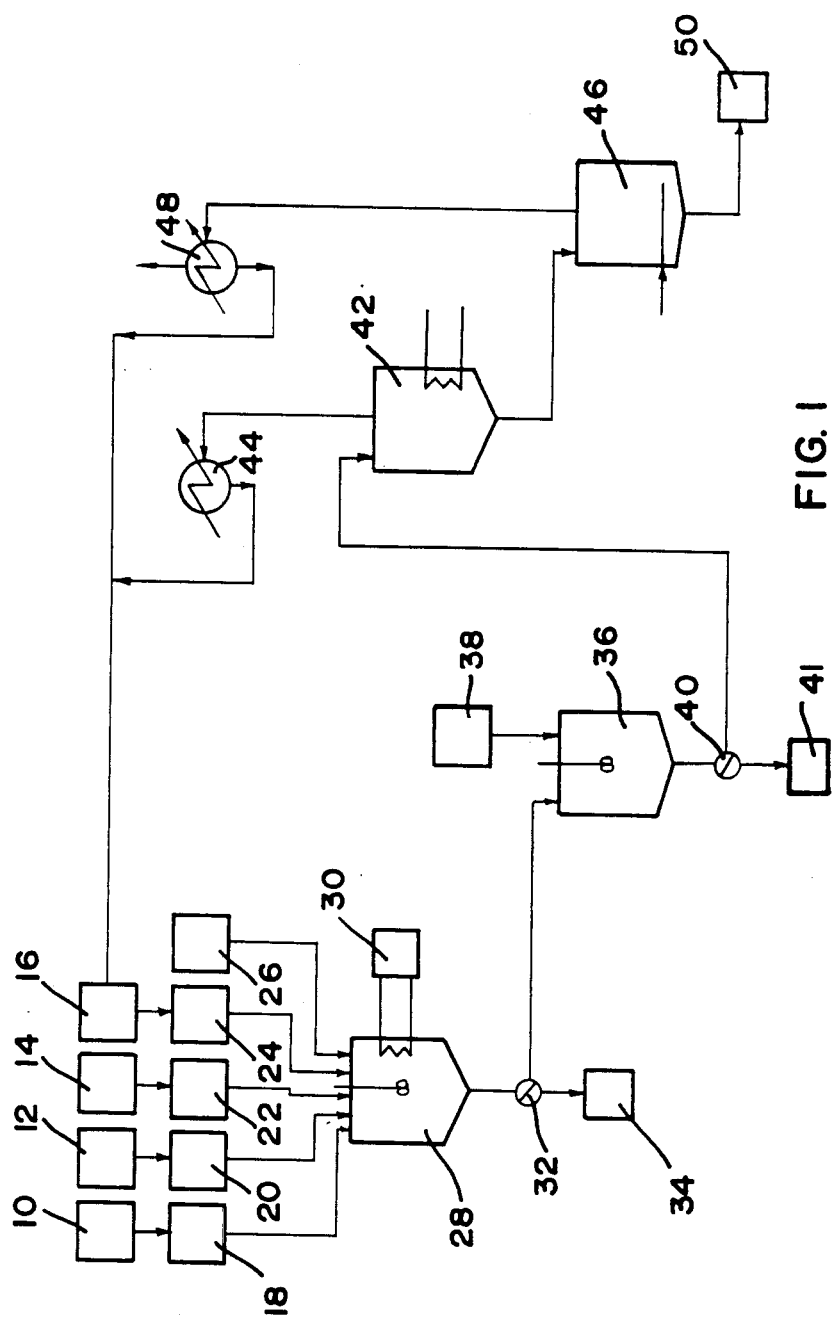
FIGS. 1–4 show apparatus for carrying out the process of the invention. In these drawings.
Figure 2:
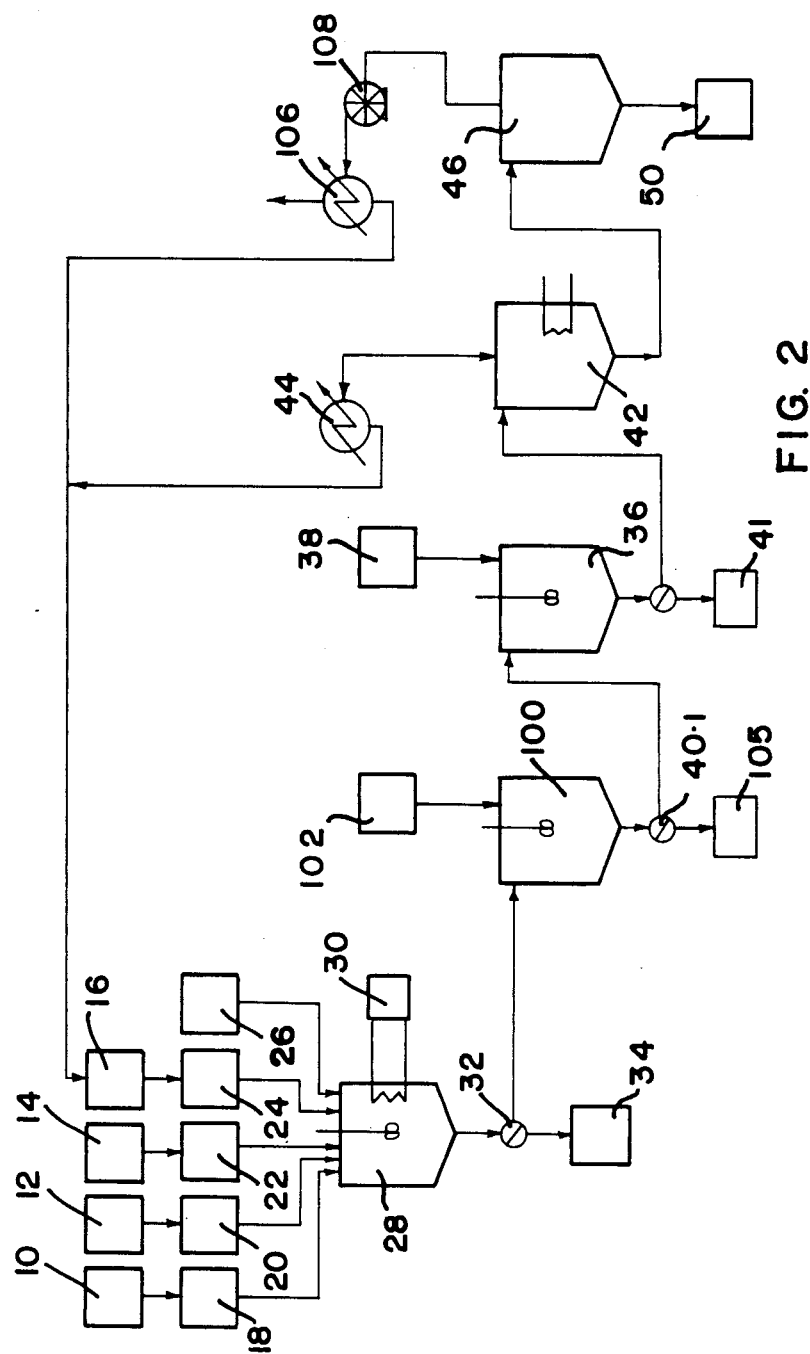

In FIGS. 1 and 2, substrate storage tank, nitric acid storage tank, sulphuric acid storage tank, and solvent storage tanks are shown at 10, 12, 14 and 16 respectively. These lead to substrate, nitric acid, sulphuric acid and solvent head tanks 18, 20, 22 and 24 respectively. A dump water head tank is shown at 26.

The head tanks lead to a nitration reactor 28 cooled by a refrigeration unit 30. The outlet from the nitration reactor 28 leads to a phase separator 32, and from there to both a used acid storage/disposal vessel 34 and a neutraliser 36 supplied by a neutralisation liquor tank 38 (FIG. 1) or a wash vessel 100 supplied by a dump tank 102 (FIG. 2), and then to a phase separator 40.

Referring now only to FIG. 1, one outlet from the phase separator 40 leads to effluent storage/disposal tank 41 while the other outlet leads to an atmospheric-pressure stripping tank 42 and from there to an air-stripping tank 46 and final product storage tank 50.

A further outlet from the atmospheric-pressure stripping tank 46 leads to an atmospheric condenser 44 and from there it leads both to the solvent storage tank 16 and to a refrigerated condenser 48, and then to the air-stripping tank 46.

Referring now only to FIG. 2, one outlet from the phase separator 40 leads to a weak acid water storage/disposal tank 105, while the other outlet leads to neutraliser 36 fed by neutralising liquor tank 38. The outlet from the neutraliser 36 leads to phase separator 40.1. One pipe leads from here to effluent storage/disposal tank 41 while the other pipe leads to atmospheric-pressure stripping tank 42.

The outlet from the atmospheric-pressure stripping tank 42 leads to vacuum-stripping tank 46 and thence to the final product storage tank 50. A pipe from the atmospheric-pressure stripping tank 42 leads through atmospheric condenser 44 and from there to both the solvent storage tank 16 and a vacuum stripper solvent condenser 106. The vacuum stripper solvent condenser has a pipe leading through a vacuum pump 108 to the vacuum-stripping tank 46.

Figure 3:
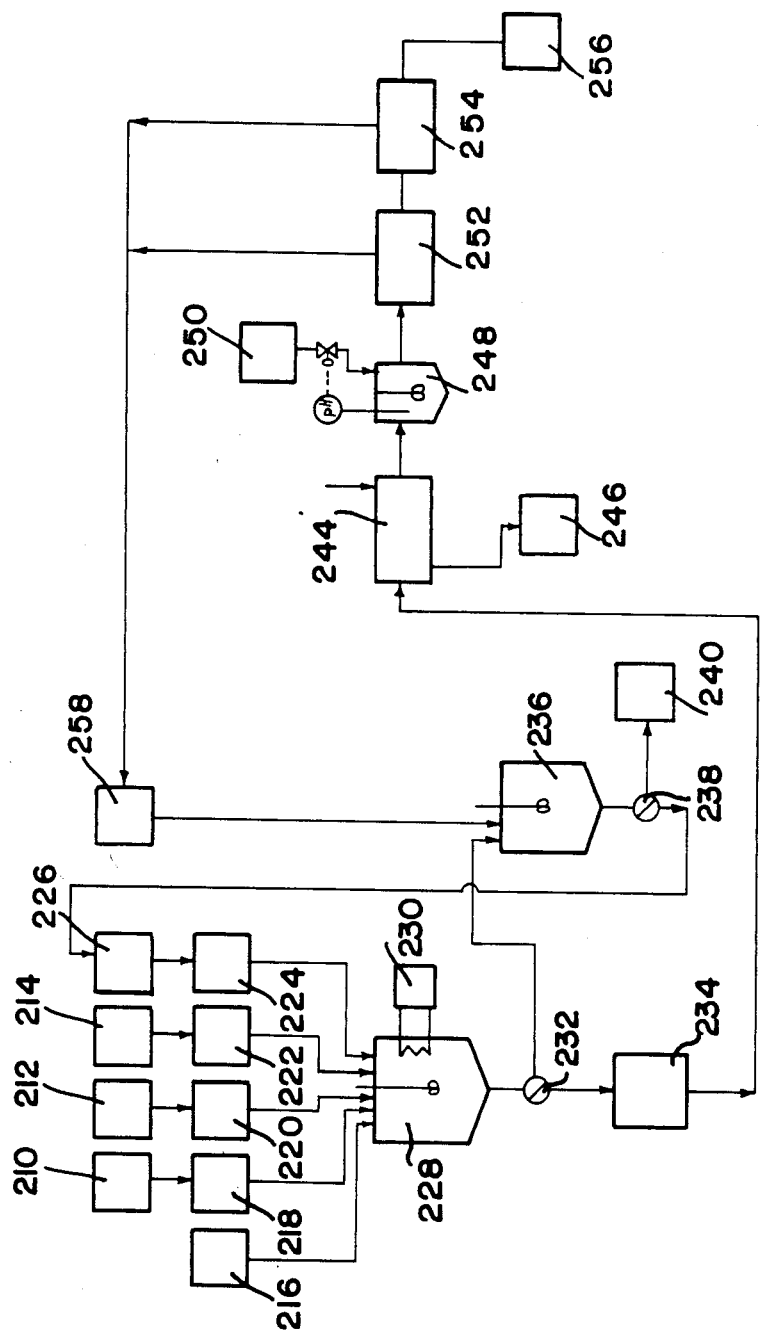

In FIG. 3, substrate, nitric acid, sulphuric acid, and acid-washed solvent storage tanks are shown at 210, 212, 214 and 216 respectively. A dilution water storage tank is shown at 216. Head tanks for substrate, nitric acid, sulphuric acid and solvent are shown at 218, 220, 222 and 224 respectively. An acid-washed solvent storage tank is shown at 226. A nitration reactor 228 is cooled by a refrigeration unit 230. The outlet from the nitration reactor 228 leads through a phase separator 232 to a buffer hold tank 234 and an acid wash tank 236.

The outlet from the acid wash tank 236 leads through a phase separator 238 to a by-product sulphuric acid storage tank 240 and to the acid-washed solvent storage tank 226.

The outlet from the buffer hold tank 234 leads to a countercurrent multistage wash unit 244, from which outlets leads to a by-product nitric acid storage 246 and a neutraliser 248 fed by a neutralising liquor tank 250.

The outlet from the neutraliser 248 leads to first and second stage stripping units 252 and 254 and, from these units to the final product storage 256 and to a fresh and recovered solvent storage tank 258. From here solvent can pass to the acid wash tank 236.

Figure 4:
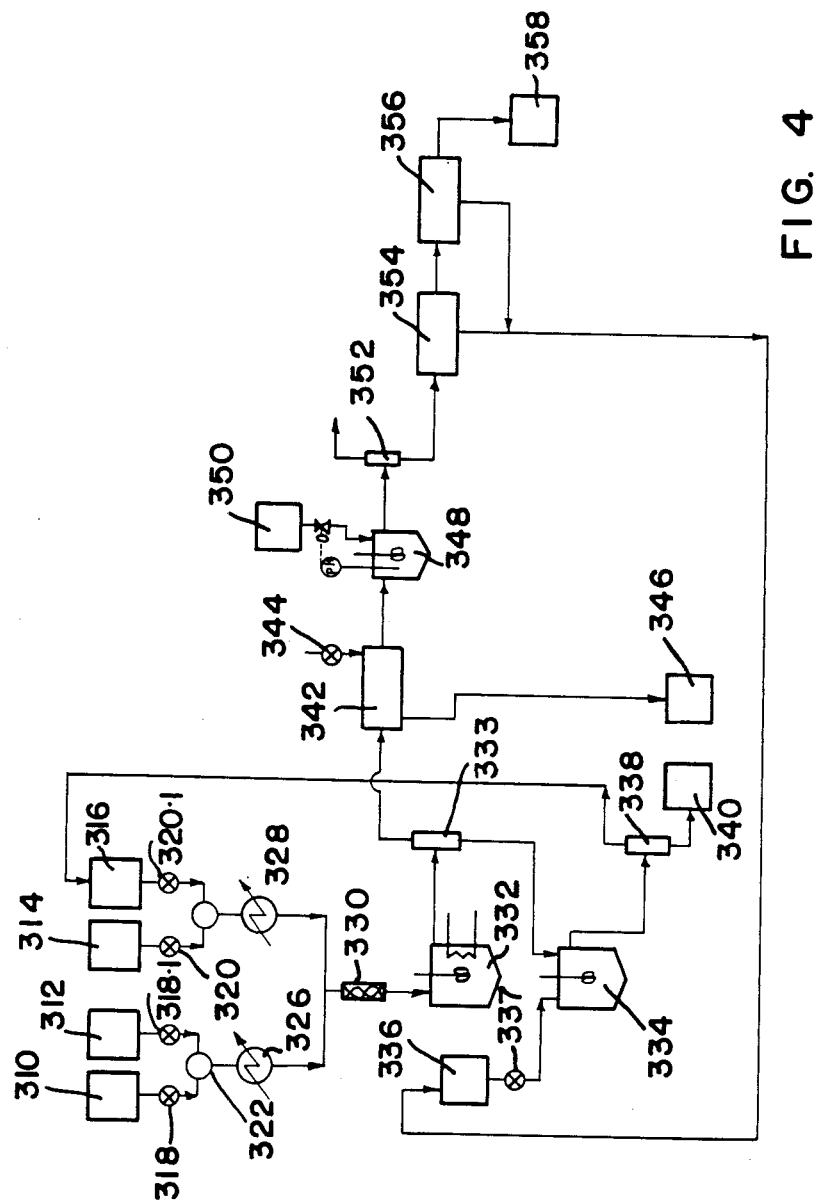

In FIG. 4, nitric acid, sulphuric acid, substrate and solvent storage (after acid wash) tanks are shown at 310, 312, 314 and 316 respectively. Metering devices are shown at 318, 318.1, 320 and 320.1. These lead through mixers 322 and 324 to acid coolers 326 and 328 and then to reactor 330.

The outlet from the reactor 330 leads to a reaction hold-up tank 332 and then to a phase separator 333. One phase is led to acid wash vessel 334, which is also fed from a recovered solvent tank 336 through a metering device 337.

The outlet from the acid wash vessel 334 leads through a phase separator 338 to a spent sulphuric acid storage tank 340 and the solvent storage tank 316.

The other phase from the phase separator 333 is led through a countercurrent water wash unit 342, into which water is metered through 344, and then to a neutraliser 348 fed by a neutralising liquor tank 350. The outlet from the neutralising liquor tank 359 leads to a phase separator 352 and then to stripping units 354 and 356 to final product storage tank 358.

A pipe leads from the stripping units 354 and 356 to the recovered solvent tank 336.

A more detailed explanation of the working of the various apparatus will now be given. Pumps, compressors, valves and the like are also not included.

FIG. 1 utilizes batch nitration, followed by spent sulphuric acid separation, aqueous neutralisation and atmospheric-air solvent recovery. The process is entirely a batch operation and, while the various process steps are shown as occurring in different vessels, it is possible to carry out all the operations in a single suitably equipped reactor or to combine some of the process steps, thus using fewer vessels. The process is best suited to reactions utilizing 100 to 110% of the stoichiometric amount of nitric acid.

The operations in this process are as follows: Fixed volume head tanks 18, 20, 22, 24 are filled with substrate, nitric acid, sulphuric acid and solvent respectively, from storage tanks 10, 12, 14, 16. Head tank 26 can be filled with fresh water. Head tanks 20, 22 and 24 are then discharged into the reactor and cooled to the desired reaction temperature. The substrate is then fed into the reactor at such a rate that the cooling is just sufficient to maintain the desired reaction temperature. When all the substrate has been added, the contents of head tank 26 are discharged into the reactor, and the mixture is agitated for 10-30 minutes. After this, agitation is stopped and the phases allowed to separate.

The organic phase, containing the solvent, product and traces of nitric acid is discharged via the phase separator 32 to the neutraliser 36. The aqueous phase, containing water, sulphuric acid and some nitric acid, is discharged to storage for further treatment, disposal, or sale. The contents of the neutraliser are now neutralised to pH 7-9, using aqueous 1-5% ammonium hydroxide or other suitable alkali: when the aqueous phase pH is 7-9, agitation is stopped and the phases allowed to separate. The organic phase (solvent and product) will be the lower phase. This is pumped via phase separator 40 to stripper 42. The supernatant aqueous phase, substantially water with small quantities of ammonium nitrate, is pumped to storage and disposal.

In stripper 42, the solution is boiled until the temperature reaches 80°-120° C., the solvent being condensed in condenser 106 and returned to solvent storage. The resulting solution, 70-90% product is passed to the stripper 46 where it is further stripped of solvent using a stream of air sparged into the vessel. The solvent laden air is vented via a condenser to recover some of the solvent.

The product, containing 0-2% solvent, is pumped to storage. In this process, the nitric acid excess over the stoichiometric reaction requirement should not exceed 10%.

As mentioned above, all of the operations can be carried out in reactor 28, if the vessel is equipped to allow decanting of the upper phase. This may be achieved, for example, by having suitably placed off-take nozzles on the side of the vessel. While fixed volume head tanks are used in the example to ensure accurate metering of the reactants, any other suitable method can be used.

FIG. 2 utilizes batch nitration, followed by separation of spent sulphuric acid, a second wash to recover nitric acid, neutralisation and atmospheric-vacuum solvent recovery. The process is entirely a batch operation and, while the various process steps are shown as occurring in different vessels, it is possible to carry out all of the steps in a single suitably equipped reactor, or to combine some of the steps thus using fewer vessels.

The process is best suited to reactions using 120 to 220% of the stoichiometric amount of nitric acid.

The operations in this process are as follows: Fixed volume head tanks 18, 29, 22, 24 are filled with substrate, nitric acid, sulphuric acid and solvent respectively, from storage tanks 10, 12, 14, 15. Head tank 104 which is optional, is filled with fresh water. Head tanks 20, 22, 24 are then discharged into the reactor 28 and cooled to the desired reaction temperature. The substrate is then fed into the reactor at such a rate that the cooling is just sufficient to maintain the desired reaction, temperature. When all the substrate has been added, the contents of head tank 104 are discharged into the reactor 28, and the mixture is agitated for 10-30 minutes. After this, agitation is stopped and the phases allowed to separate.

The organic phase, containing the solvent, product and substantially all of the excess nitric acid, is discharged via the phase separator 32 to the wash vessel 100, while the aqueous phase, containing water, sulphuric acid and traces of nitric acid is discharged to storage for further treatment, disposal or sale.

The organic phase is now washed with the water from the second dump tank 102. The organic phase resulting from this operation is solvent and product with traces of residual nitric acid. This phase is transferred to the neutraliser 36 via the phase separator. The aqueous phase, which is 2 to 20% nitric acid, is transferred to storage tank 105.

The organic phase in the neutraliser 36 is neutralised with 1-5% ammonium hydroxide or other suitable alkali, until the pH of the aqueous phase is 7-9. The neutralised organic phase (solvent and product) is transferred via the phase separator, to the stripper 42 The aqueous phase containing small amounts of ammonium nitrate, is transferred to the storage/disposal tank 41 for the next batch.

In stripper 42, the, solution is boiled until the temperature reaches 80°-120° C., the solvent being condensed in condenser 106, and returned to solvent storage The resulting solution, 70-90% product is passed to stripper 46 where it is further stripped of solvent by heating under vacuum provided by vacuum pump 108 This process can be used for any of the reactant proportions according to the invention, although it is best suited for reactions utilising 120-220% (preferably 150-220%) of the stoichiometric reaction requirement of nitric acid.

As mentioned above, all of the operations can be carried out in reactor 28, if the vessel is equipped to allow decanting of the upper phase This ma be achieved, for example, by having suitably placed offtake nozzles on the side of the vessel While fixed volume head tanks are used in the example to ensure accurate metering of the reactants, any other suitable method can be used FIG. 3 describes a semi-continuous process, utilising batch nitration and sulphuric acid wash, with continuous nitric acid recovery, neutralisation and solvent recovery.

This process can be used for any of the reactant proportions according to the invention, but if the nitric acid excess is less than 10%, it is possible to omit the nitric acid recovery step.

The operations in this process are as follows: Fixed volume head tanks 218, 220, 222, 224 are filled with substrate, nitric acid, sulphuric acid and solvent from storage tanks 210, 212, 214, 216 respectively. Head tanks 216 are filled with dilution water if the process being used calls for dilution after nitration. Head tanks 220, 222, 224 are then discharged into the reactor and cooled to the desired reaction temperature. The substrate is then fed into the agitated reactor at such a rate that the cooling is just sufficient to maintain this temperature. When all the substrate has been added, head tank 216 is discharged into the reactor and agitation is maintained for 10-30 minutes. After this, agitation is stopped and the phases allowed to separate. The aqueous phase, containing the sulphuric acid, water and traces of product, solvent and nitric acid, will be the lower phase.

This phase is discharged to the acid wash vessel 236, where it is washed with 0.5-2.0 volumes of fresh and recovered solvent. The washed acid will contain negligible amounts of product and nitric acid, but will be saturated with solvent, which may be removed by airstripping. The wash solvent will now contain traces of product and nitric acid and is transferred to storage tank 226 for the next batch.

The organic phase from reactor 228 is discharged to a hold tank 234 and from there, fed continuously to the countercurrent water wash unit 244. This can be any form of continuous countercurrent liquid/liquid contacting device with preferably 3-10 equilibrium stages. The amount of water fed to this unit is controlled such that nitric acid of between 30-60% is recovered. This nitric acid will be saturated with solvent which can be removed, for example, by air-stripping. The nitric acid by-product may be disposed of, sold or reconcentrated to 98% for return to the nitration.

The organic product from unit 244 will contain traces of residual acidity which is neutralised in the neutraliser 248. The neutralisation can be achieved using an organic alkali, in which case no phase separation is required, or with an aqueous alkali such as 1-5% ammonia solution, in which case the neutraliser must be followed by a phase separator to remove the neutralising liquor.

The organic product from the neutraliser will be a 10-30% solution of product in the solvent. The solvent can be recovered by any of the solvent recovery techniques described above.

FIG. 4 illustrates a continuous process utilising continuous nitration, sulphuric acid wash, strong nitric acid recovery, neutralisation and solvent recovery.

This process can be used for any of the reactant proportions according to the invention, but if the nitric acid excess over the stoichiometric reaction requirement is low, i.e. less than 10%, the strong nitric acid recovery process step can be omitted.

The operations in this process are as follows: Nitric and sulphuric acids from head tanks 310 and 312 are metered (using any suitable accurate metering device, such as metering pumps or overflowing head tanks) to a mixer and then to a cooler where the mixed acid is cooled to the desired reaction temperature. Similarly, solvent and substrate are metered, mixed and cooled. The two streams now pass to the continuous reactor 330 and thence to the hold-up tank 332. The combination of reactor 330 and hold-up tank 332 can be any suitable form of continuous two-phase reaction system providing adequate mixing, cooling and residence time. From the nitration section, the mixed stream passes to a phase separation which can be any suitable continuous phase separation device. The stream can, optionally, be diluted with a suitable quantity of water before the phase separator to adjust the water to spent sulphuric acid mole ratio.

The spent sulphuric acid from the phase separator passes to the wash vessel 334 into which is metered fresh and recovered solvent at the required rate. From the wash vessel, the mixture of solvent and spent acid is passed to a phase separation device where the spent sulphuric acid is drawn off to storage, and the wash solvent is returned to solvent storage for the nitration reaction.

The solution of solvent, product and nitric acid is passed from the phase separator 333 to the continuous nitric acid recovery stage. This can be any suitable countercurrent multi-stage liquid/liquid contacting device where the organic solution is washed by a countercurrent stream of water. The resulting aqueous phase will be nitric acid of up to 65% concentration, which is sent to storage or further treatment and recycled as fresh nitric acid. The organic phase, with low residual acidity, is sent to the neutraliser 348, where it is contacted with either an aqueous alkali solution, in which case the neutraliser should be followed by a phase separator, or it is neutralised with an organic alkali material.

Following neutralisation, the organic stream will be a solution of product in the solvent. This stream is passed to the solvent recovery stages 354 and 356, where the solvent is stripped off and returned to the sulphuric acid wash section. The recovery process can be any of the processes described above.

The following non-limiting examples illustrate the invention:

EXAMPLE 1

To 800 ml dichloromethane were added 112 g 98% $H_2SO_4$ (1.12 moles) and 129 g 98% $HNO_2$ (2.00 moles, i.e. 200% of the stoichiometric requirement). 130 g iso-octanol (1.00 moles) were then slowly added to the well-agitated mixture whilst maintaining the temperature between 0° C. and 5° C. The FWSR of the reaction was 1.13. Water (385 ml) was then added to reach a WSSA of 20, and the aqueous spent acid separated from the mixture. This spent acid contained the majority of the excess nitric acid and the sulphuric acid used in the reaction. The organic layer containing the product was washed once with 385 ml water to remove most of the residual nitric acid, a further 385 ml water added and the mixture neutralised to pH 6-8 with 25% ammonia solution. After separation, the solvent was removed from the organic layer using a rotary evaporator at 60° C. under approximately 25 torr water vacuum. 175 g product was recovered, which represents 100% yield based on the alcohol.

Infra-red spectroscopy of the product confirmed its identity as iso-octyl nitrate, and showed that it was essentially pure, i.e. free of residual solvent, unnitrated material and oxidised by-products.

EXAMPLE 2

The procedure of Example 1 was repeated, using 600 ml dichloromethane, 121 g 98% $H_2SO_4$ (1.21 moles to give an FWSR of 1.00), 67.5 g 98% $HNO_3$ (1.05 moles, i.e. 105% of the stoichiometric requirement) and 102 g n-hexanol (1.00 moles) Nitration was carried out at 5°-10° C., and the spent acid separated at a WSSA of 20. 144 g n-hexyl nitrate was recovered (98.0% yield). Infra-red spectroscopy confirmed its identity, and showed that it was free of solvent, hydroxylic material or oxidised by-products.

EXAMPLE 3

105 g 98% $H_2SO_4$ (1.05 moles, to give an FWSR of 1.13), 64.3 g 98% $HNO_3$ (1.02 moles, i.e. 102% of the stoichiometric requirement) and 130 g iso-octanol (1.00 moles) were reacted together in the presence of 550 ml dichloromethane, using the procedure of Example 1. The reaction temperature was maintained between 5° and 10° C. No water was added prior to separation of the spent acid, which was thus removed at a WSSA of 1.13. This spent acid comprised essentially strong sulphuric acid, and was stable (i.e. no exothermic decomposition) for more than 48 hours at ambient temperature (20°-30° C.). The organic layer was washed, neutralised, and stripped of solvent as in Example 1, to give 171.8 g pure product (98.2% yield). Infra-red spectroscopy confirmed its identity as iso-octyl nitrate, free of impurities, such as solvent, unreacted iso-octanol, or oxidised by-products.

EXAMPLE 4

Using the procedure of Example 1, butoxy-ethyl nitrate was prepared, using 400 ml dichloromethane, 88.4 g (0.75 mole) butoxyethanol, 95.9 g (1.49 moles) 98% $HNO_3$ (200% of the stoichiometric) and 45.3 g (0.45 moles) 98% $H_2SO_4$ (to give an FWSR of 2.00). 146 ml water was added to separate the spent acid at a WSSA of 20. This spent acid contained the majority of the excess nitric acid and the sulphuric acid used in the reaction. The organic layer was neutralised and stripped, as in Example 1. A yield of 120.8 g product was obtained (98.8% of theoretical), which was shown by infra-red spectroscopy to be butoxyethyl nitrate, free of solvent, hydroxylic material or oxidised by-products.

EXAMPLE 5

To 120 ml dichloromethane were added 66 g 98% $H_2SO_4$ (0.66 moles, the requirement for FWSR=1.47), 12.6 g 100% nitric acid (0.20 moles, the stoichiometric requirement) and 25.2 g 50% nitric acid (0.20 moles, to supply 200% of the stoichoimetric requirement). 15 g triethylene glycol (0.10 moles) were then slowly added to the well-agitated mixture whilst maintaining the temperature between 0° C. and 2° C. Stirring was stopped, and the mixture allowed to separate. The lower spent acid (comprising mainly strong sulphuric acid) was removed. This spent acid was stable for more than 48 hours at ambient temperature. The organic layer was washed three times with 20 ml aliquots of water to remove the excess nitric acid, then washed with 50 ml water, after which it was neutral. Solvent was removed on a rotary evaporator at 60° C. and 25 torr, to give 23.2 g product (97% yield). Infra-red spectroscopy confirmed the product as triethylene glycol dinitrate, free of solvent, hydroxylic material, or oxidation by-products.

EXAMPLE 6

A number of experiments were conducted, using the following process:

To 1000 ml dichloromethane were added 150 g 98% $H_2SO_4$ (1.5 moles, requirement for FWSR of 1.63) and 257 g 98% $HNO_3$ (4.0 moles, i.e. 200% of the stoichiometric requirement). 150 g triethylene glycol (1.00 moles) dissolved in 300 ml dichloromethane were then slowly added to the well-stirred mixture whilst maintaining a temperature of 0°-2° C. This addition required about 20 minutes. A 15 minute post-reaction period was allowed before adding 24.5 ml water (for a WSSA of 2.54). Agitation was stopped, and the phases allowed to separate. The lower spent acid layer (comprising mainly strong sulphuric acid) was removed, leaving an organic layer comprising dichloromethane, product, and the majority of the excess nitric acid. This organic layer was washed with 3×100 ml aliquots of water to remove the nitric acid, then a further 100 ml water added, and the mixture neutralised with 25% ammonia solution. The aqueous layer was removed, and the solvent stripped from the product on a rotary evaporator at 60° C. and 25 torr vacuum. Six repeat experiments gave yields in the range 98.0 to 99.8% of theoretical. All products were confirmed to be triethylene glycol dinitrate by infra-red spectroscopy, and were shown to be free of solvent, hydroxylic materials or oxidation by-products.

EXAMPLE 7 To 150 ml chloroform were added 25.7 g 98% nitric acid (0.4 moles, 200% of the stoichiometric), and 25.7 g 98% sulphuric acid (0.26 moles, requirement for FWSR=1.0). 24.4 g (0.2 moles) butoxyethanol were then added slowly with good agitation whilst maintaining the temperature between −10° C. and +4° C. 88 ml water was then added to the mixture to achieve a WSSA of 20. The organic layer was separated, washed twice with 60 ml water, then neutralised and stripped of solvent on a rotary evaporator. 33.0 g butoxyethyl nitrate was recovered (98.8% of theoretical), which was shown by infra-red spectroxcopy to be free of solvent, hydroxylic material, or oxidation by-products.

EXAMPLE 8

Commercial Scale Example

This is an example of commercial scale manufacture of iso-octyl nitrate using the apparatus of FIG. 1. The process is operated with 103% of the stoichiometric amount of nitric acid. The acids used are 98% $H_2SO_4$ and 96% $HNO_3$. The FWSR was 1. There were 550 ml of solvent (dichloromethane) per mole of hydroxy group of the isooctyl alcohol. Operations are as follows:

Head tank 18 is filled with 731 kg of iso-octyl alcohol, head tank 20 is filled with 378 kg 96% nitric acid, head tank 22 is filled with 752 kg 98% $H_2SO_4$, and head tank 24 is filled with 4100 kg DCM. Head tanks 20, 22, 24 are discharged into the 7000 liters stainless steel reactor and cooled to 5° C., using refrigerated DCM in coils in the reactor. Agitation is provided by a double impellor turbine agitator. The iso-octyl alcohol is then fed into the reactor under temperature control, the whole nitration taking 70 minutes. At the end of this time, the agitator is stopped and the phases allowed to separate. The bottom phase, which is 84.5% $H_2SO_4$ with traces of nitric acid and solvent, is separated and sent to disposal.

The organic phase is then neutralized with approximately 15 kg 25% ammonia in 1200 liters water, and the phases are again separated.

The organic phase is now steam-stripped by heating with 50 kPa(g) steam in coils in the stripper. When the liquid temperature reaches 90° C., air is sparged into the vessel, with the temperature maintained at 80°–90° C. until the analysis of the product shows less than 0.5% DCM. The product is cooled and transferred to storage. The average product quantity is 964 kg which is 98% yield. The operations are shown as taking place in different vessels but they are in fact carried out in the reactor.

EXAMPLE 9

To 1000 ml of dichloromethane there were added 152.4 g 98% $H_2SO_4$ (1.52 moles) and 257.2 g 98% $HNO_3$ (4 moles, i.e. 200% of the stoichiometric requirement). 106 g diethylene glycol (1 mole) was then added slowly to the well-agitated mixture whilst maintaining the temperature between 0° C. and 5° C. The FWSR of the reaction was 1.5. Water (507 ml) was then added to reach a WSSA of 20, and the aqueous spent acid separated from the mixture. This spent acid contained the majority of the excess nitric acid and the sulphuric acid used in the reaction. The organic layer containing the product was washed once with 300 ml water to remove most of the residual nitric acid, a further 300 ml water was added and the mixture neutralized to pH 6–8 with 25% ammonia solution. After separation, the solvent was removed from the organic layer using a rotary evaporator at 60° C. under approximately 25 torr vacuum. 191.4 g product was recovered, which represents 99.7% yield based on the diol.

Infra-red spectroscopy of the product confirmed its identity as diethylene glycol dinitrate, and showed that it was essentially pure, i.e. free of residual solvent, unnitrated material and oxidised by-products.

We claim:

1. Process for the preparation of nitric acid esters of organic hydroxyl compounds selected from the group consisting of alkylene glycol monoalkyl ethers, polyalkylene glycol monoalkyl ethers and polyalkylene glycols in which at least 92% of the organic hydroxyl compound is converted to a nitric acid ester selected from the group consisting of alkylene glycol monoalkyl ether mononitrates, polyalkylene glycol monoalkyl ether mononitrates and polyalkylene glycol nitrates, which process comprises the steps of:
   (1) reacting the organic hydroxyl compound with nitric acid in an amount of from 180% to 220% of the stoichiometric requirement for complete nitration in the presence of sulphuric acid in such an amount that the mole ratio of water to sulphuric acid (FWSR) at the end of the reaction is from 0.2:1 to 2.5:1 and in the presence of an organic solvent which is inert to the reaction conditions in an amount of 200 to 2000 ml per mole of hydroxyl group, followed by
   (2) separating off first of all a spent acid comprising substantially sulphuric acid and water from the reaction mixture, leaving substantially all the unreacted nitric acid in solution in the organic solvent,
   (3) washing the remaining reaction mixture after removal of the sulphuric acid to remove nitric therefrom as a separate solution from the already separated sulphuric acid and to leave the solvent containing the desired nitric acid esters,
   (4) substantially neutralizing the residual acidity of the organic solvent solution, and
   (5) removing the solvent to leave the nitric acid ester.

2. A process as claimed in claim 1, wherein the nitric acid ester is selected from poly(oxyethylene)glycol dinitrate oligomers and mixture thereof.

3. A process as claimed in claim 1, wherein the nitric acid ester is selected from diethylene glycol dinitrate, triethylene glycol dinitrate and poly(oxyethylene)-glycol dinitrates mixtures containing 4 to 10 oxyethylene groups.

4. A process as claimed in claim 1, wherein the inert organic solvent is dichloromethane.

* * * * *